US00PP35258P2

(12) United States Plant Patent
Whitehouse et al.

(10) Patent No.: US PP35,258 P2
(45) Date of Patent: Jul. 11, 2023

(54) ***FRAGARIA* PLANT NAMED 'EMR 639'**

(50) Latin Name: *Fragaria x ananassa*
Varietal Denomination: EMR 639

(71) Applicant: NIAB, Cambridge (GB)

(72) Inventors: Adam Barrie Whitehouse, Kent (GB); David William Simpson, Taunton (GB); Abigail Johnson, Kent (GB)

(73) Assignee: NIAB, Cambridge (GB)

( * ) Notice: Subject to any disclaimer, the term of this patent is extended or adjusted under 35 U.S.C. 154(b) by 0 days.

(21) Appl. No.: 17/979,136

(22) Filed: Nov. 2, 2022

Related U.S. Application Data

(60) Provisional application No. 63/276,326, filed on Nov. 5, 2021.

(51) Int. Cl.
*A01H 5/08* (2018.01)
*A01H 6/74* (2018.01)

(52) U.S. Cl.
USPC ..... Plt./209

(58) Field of Classification Search
USPC ..... Plt./208, 209
See application file for complete search history.

(56) References Cited

PUBLICATIONS http://berryplantsltd.co.uk/whats-new/—Retrieved from the website on Feb. 23, 2023.*
https://www.niab.com/malling-fruits/strawberries/malling%E2%84%A2-supreme—Retrieved from the website on Feb. 23, 2023.*

* cited by examiner

*Primary Examiner* — Susan McCormick Ewoldt
(74) *Attorney, Agent, or Firm* — Penny J Aguirre

(57) ABSTRACT

A new cultivar of *Fragaria* plant named 'EMR 639' that is characterized by its semi-upright growth habit, its large leaf size, its flower diameter that is large in size, its calyx and corolla that are similar in width, its flower petals that are white in color, its berries that are equal in length and width, medium to large in size, predominately conical in shape, and medium red in color with achenes that are positioned below the surface (sunken), its calyx that is level with the fruit, its sepals that are held upwards, its calyx diameter that is slightly smaller in relation to the fruit size, its early flowering time and fruit ripening time, and its fully remontant fruit bearing habit.

2 Drawing Sheets

Botanical classification: *Fragaria* x *ananassa*.
Variety denomination: 'EMR 639'.

BACKGROUND OF THE INVENTION

The present invention relates to a new and distinct cultivar of *Fragaria*, botanically known as *Fragaria* x *ananassa* and will be referred to hereafter by its cultivar name, 'EMR 639'. 'EMR 639' is a day neutral strawberry plant primarily adapted to the climate and growing conditions of the United Kingdom and other regions of similar climate and day length.

The new cultivar was derived from an ongoing breeding program conducted by the Inventors at a farm in Kent, United Kingdom. The objective of the breeding program was to develop a new cultivar of *Fragaria* with desirable characteristics including fruit size, fruit shape, and skin firmness. 'EMR 639' arose from a controlled cross made by the Inventors in February of 2010 between *Fragaria* 'Finesse' (not patented) as the female parent and an unpatented selection from the Inventor's breeding program, designated as accession number 'EMR 399' as the male parent. 'EMR 639' was selected as a single unique plant in July of 2011 from amongst the seedlings that resulted from the above cross.

Asexual propagation of the new cultivar was first accomplished by rooting stolons in Kent, United Kingdom in July of 2014. Asexual propagation by rooting of stolons and meristem tissue culture using meristematic tissue has shown that the unique characteristics of the new cultivar are stable and reproduced true to type in successive generations.

BRIEF SUMMARY OF THE INVENTION

The following traits have been repeatedly observed and represent the characteristics of the new cultivar. These attributes in combination distinguish 'EMR 639' as a new and unique cultivar of *Fragaria*.

1. 'EMR 639' exhibits a semi-upright growth habit.
2. 'EMR 639' exhibits a large leaf size.
3. 'EMR 639' exhibits flower diameter that is large in size.
4. 'EMR 639' exhibits calyx and corolla at are similar in width.
5. 'EMR 639' exhibits flowers with petals that are white in color.
6. 'EMR 639' exhibits berries that are equal in length and width.
7. 'EMR 639' exhibits berries that are medium to large in size.
8. 'EMR 639' exhibits berries that are predominately conical in shape.
9. 'EMR 639' exhibits berries that are medium red in color.
10. 'EMR 639' exhibits achenes that are positioned below the surface.
11. 'EMR 639' exhibits a calyx that is level with the fruit.

12. 'EMR 639' exhibits sepals that are held upwards.
13. 'EMR 639' exhibits a calyx diameter that is slightly smaller in relation to the fruit size.
14. 'EMR 639' exhibits an early flowering time.
15. 'EMR 639' exhibits an early ripening time.
16. 'EMR 639' exhibits a fully remontant fruit bearing habit (everbearing).

The female parent 'Finesse' is similar to 'EMR 639' in having an everbearing, extended crop season with similar skin color. The female parent 'Finesse' differs from 'EMR 639' in having a less upright habit that is less vigorous and more compact, a lower soluble sugar score (Brix) (10° 'EMR 639' versus 7.9° 'Finesse'), a conic fruit shape, a higher density of seeds, and fruit surfaces that are less glossy. The male parent of 'EMR 639' differs from 'EMR 639' in having fruit that appears uneven when ripening, a fruit surface texture that is dry and mealy, and a larger calyx diameter. 'EMR 639' can most closely be compared to the cultivar 'Malling Champion' (not patented). 'Malling Champion' is similar to 'EMR 639' in having an everbearing, an extended crop season with similar skin color. 'Malling Champion' differs from 'EMR 639' in having a lower soluble sugar score (Brix 10° 'EMR 639' versus 7.9° 'Mailing Champion'), firmer flesh, strong skin firmness, and a more compact plant habit.

BRIEF DESCRIPTION OF THE DRAWINGS

The accompanying color photographs illustrate the overall appearance and distinct characteristics of one-year-old plants of the new cultivar as grown on table-tops in coir bags under tunnels with polyethylene covers in Faversham, Kent, United Kingdom. The photographs were taken of plants that were fruiting in early July and planted in early March from a tip taken in early July the summer before and grown as a potted plant prior to planting and overwintered above 5° C.

The photograph in FIG. 1 provides a view of the fruit of 'EMR 639'.

Figure 1:
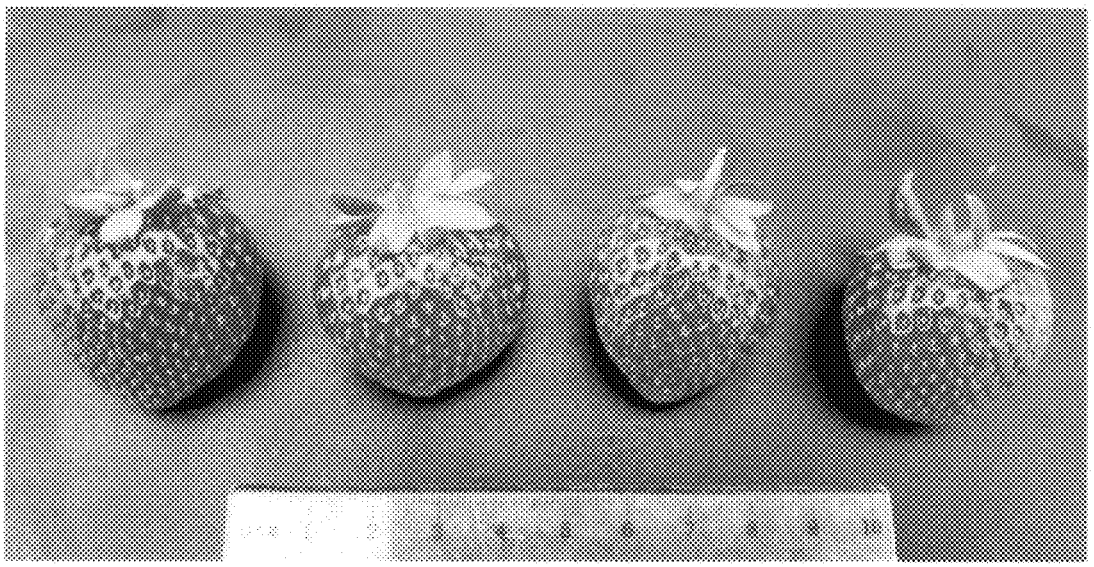
Figure 2:
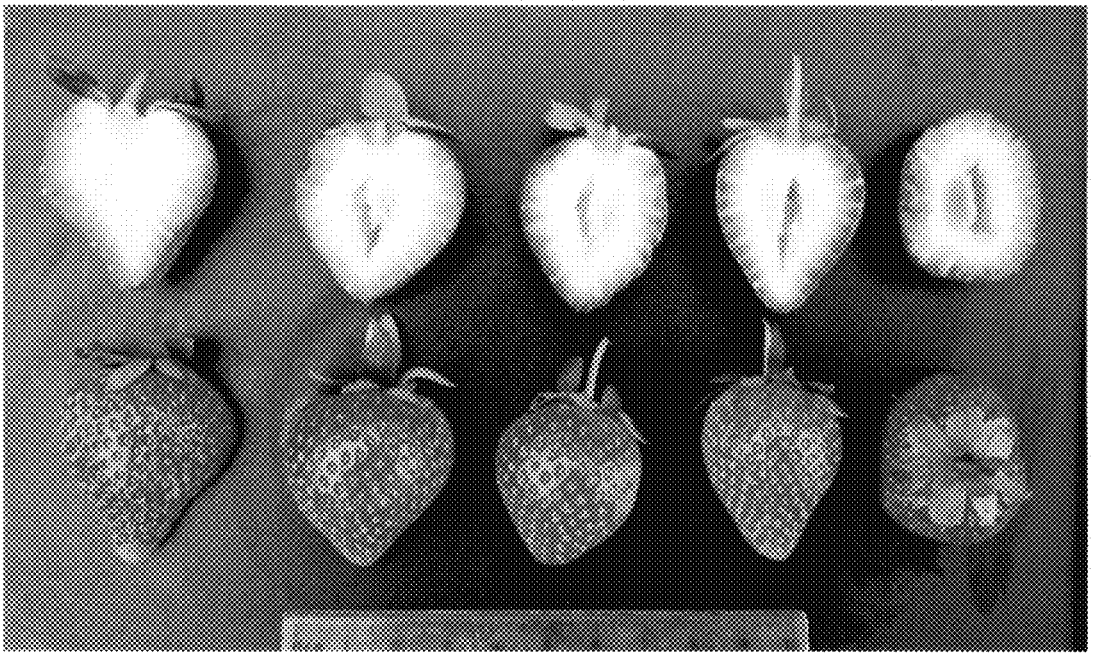

The photograph in FIG. 2 provides a view of cut fruit of 'EMR 639'.

Figure 3:
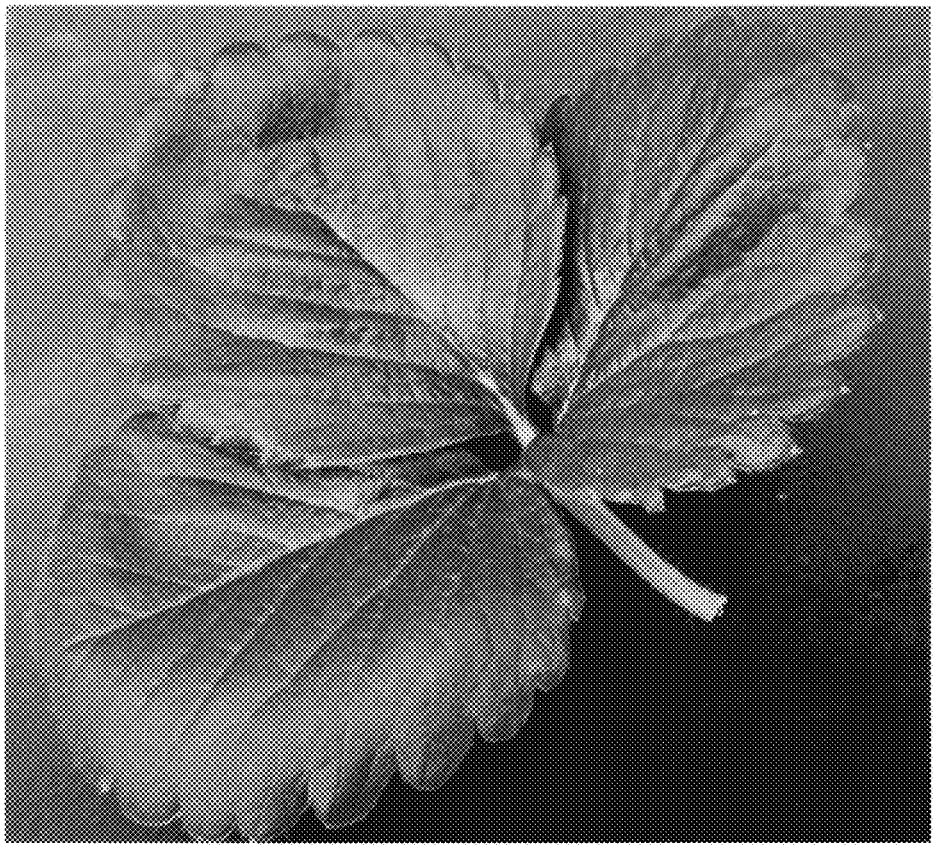

The photograph in FIG. 3 provides a view of a leaf of 'EMR 639'.

Figure 4:
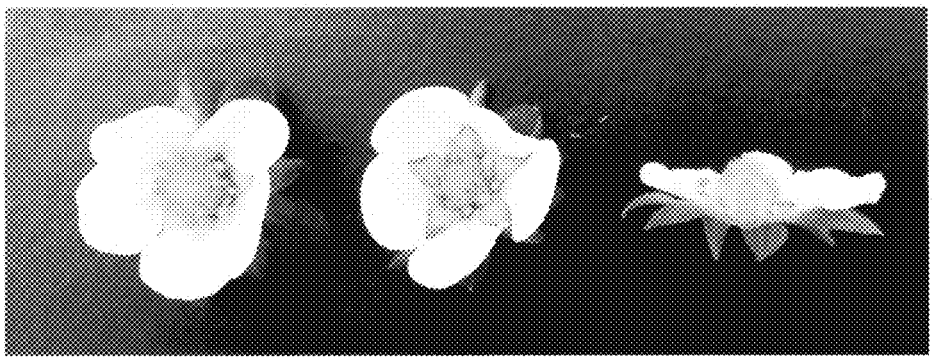

The photograph in FIG. 4 provides a close-up view of the flowers of 'EMR 639'.

The colors in the photographs are as close as possible with digital photography techniques available, the color values cited in the detailed botanical description accurately describe the colors of the *Fragaria*.

DETAILED BOTANICAL DESCRIPTION

The following is a detailed description of one-year-old plants of 'EMR 639' as grown outdoors on protected table-tops, in coir bags under tunnels with polyethylene covers in East Malling, United Kingdom. The phenotype of the new cultivar may vary with variations in environmental, climatic, and cultural conditions, as it has not been tested under all possible environmental conditions. The color determination is in accordance with The 2001 Colour Chart of The Royal Horticultural Society, London, England, except where general color terms of ordinary dictionary significance are used.

General description:

*Blooming period.*—Everbearing, continuous flower production April to September in Faversham, Kent, United Kingdom.

*Plant type.*—Herbaceous fruit producing perennial.

*Plant habit.*—Semi-upright, stoloniferous.

*Height and spread.*—Reaches about and 33.07 cm in height and 25.21 cm in width as a one-year-old plant.

*Cold hardiness.*—Not tested in areas where temperatures of less than 32° F. occur.

*Diseases and pests.*—Has shown resistance to *Phytophthora cactorum* and *Podosphaera aphanis*, and moderate resistance to *Verticillium dahlia*, no susceptibility or resistance to pests has been observed.

*Root description.*—Fibrous.

*Root development.*—An average of 2 weeks to initiate roots, fully rooted plants produced in 4 to 5 months.

*Propagation.*—Rooting of stolons and meristem tissue culture.

*Growth rate.*—Moderately vigorous.

*Stem description.*—Acaulescent.

*Stolon description.*—Average of 48.29 cm in length from crown to first daughter plant and 4.3 mm in diameter, 144C, sparse density of hairs with downward facing attitude; 1.2 mm in length, N155B in color.

Foliage description:

*Leaf division.*—Compound with three leaflets.

*Leaf arrangement.*—Basal rosettes.

*Leaf attachment.*—Petiolate.

*Leaflet shape.*—Reniform.

*Leaf color.*—Upper-side 137A and lower-side 138B with medium leaf glossiness with no leaf variegation.

*Leaf attachment.*—Petiolate.

*Leaf size.*—An average of 10.5 cm in length and 14.1 cm in width.

*Terminal leaflet.*—Length in relation to width is moderately longer.

*Terminal leaflet shape.*—Slightly cupped inwards (concave) at apex with slight blistering.

*Leaflet size.*—Average of 7.4 cm in length and 6.9 cm in width.

*Leaflet margins.*—Serrate to crenate.

*Leaflet shape in cross section.*—Concave.

*Angle of terminal leaflet to petiole.*—15 degrees.

*Leaflet base.*—Primarily obtuse.

*Leaflet apex.*—Obtuse.

*Leaflet profile.*—Slightly cupped inwards (concave) at apex with slight blistering.

*Leaflet interveinal blistering.*—Medium.

*Leaflet venation.*—Pinnate, upper surface; 145A, lower surface; 144D.

*Leaflet surface.*—Upper surface area; Matt appearance, sparse hairs across surface, main and secondary veins free of hairs, lower surface area: matte with main veins and secondary veins moderately to densely covered with very thin soft adpressed hairs.

*Leaflet surface.*—Upper surface length of 73.88 mm in length.

*Leaflet color.*—Upper surface medium green.

*Number of leaflets.*—3.

*Number of teeth on terminal leaflet.*—Average number of 18.

*Petiole.*—144B in color, average of 18.1 cm in length and 3.6 mm in diameter, attitude of hairs some slightly outward; 1.5 mm in length, and 155D in color.

*Petiolules.*—Present but very short, 145A in color, oval shaped, average of 3.06 mm in length and 1.8 mm in width, petiolules hairs dense and face outward; 1.02 mm in length and 145A in color.

*Stipules anthocyanin coloration*.—Weak.

Flower description:

*Inflorescence*.—Truss.

*Inflorescence size*.—Average of 24.58 cm (base to flower tip) in length and 7.35 cm in diameter.

*Flower initiation and expression conditions*.—Temperature dependent.

*Longevity*.—Average of one week, self-cleaning.

*Flower aspect*.—Outward to upright.

*Flower size*.—Average of 7.6 mm in height and 1.91 cm in diameter.

*Flower buds*.—6.79 mm in length to the top of the petal, 9.39 mm to the top of sepal, 5.67 mm in width.

*Flower number*.—4 per inflorescence.

*Flower fragrance*.—None.

*Calyx*.—Positioned 90° to receptacle, average of 2.8 mm in diameter and 2.96 cm in height, width of calyx is similar to corolla width.

*Sepals*.—Lanceolate in shape, an average of 10 in number per flower with an average of 1.49 cm in length and 1.52 cm in width; sepal margin is entire and 143A in color with anthocyanin absent.

*Petals*.—Average of 5, arrangement of petals is overlapping, average of 1.11 cm in length and 1.31 cm in width, petal apex shape obtuse, and petal base shape obtuse, petal margin entire, color; 155C upper surface, 155C lower surface.

*Peduncle*.—144C in color, an average of 15.53 cm in length and 3.9 mm in diameter, surface moderately covered with thin soft hairs 1.2 mm in length and NN155D in color, held at an average angle of upwards to 55°.

*Pedicel*.—145B in color, an average of 4.2 cm in length and 1.5 mm in diameter, surface densely covered with thin soft hairs 0.7 mm in length and NN155D in color, held in an upwards angle.

*Bracts*.—Average of 4 per number inflorescence, narrow elliptic to narrow ovate in shape, an average length of 8.7 mm and 4.9 mm width, color 144A and covered with pubescent hairs NN155B in color.

Reproductive organs:

*Gynoecium*.—Average of 7 mm in length, 0.1 mm in diameter, steeply dome shaped, numerous simple pistils present with capitate shaped stigma, average of 244, color; pistils 12B, stigmas 12B, receptacle 144C.

*Androecium*.—Present with an average of 24, filaments 1.7 mm in length and 3C in color, anthers 1.2 mm in length, and 0.7 mm in width, 17B in color and pollen 17B in color.

Fruit description:

*Shape*.—Predominately cordate but larger berries reniform with some conical.

*Surface*.—Slight sheen, 45A in color. Length in relation to width is moderately shorter.

*Calyx position*.—Level with the fruit.

*Diameter of calyx relative to fruit diameter*.—Slightly smaller.

*Adherence of calyx*.—Very strong.

*Glossiness*.—Medium.

*External color* (*skin*).—45A.

*Internal color*.—35A.

*Color of core*.—N155B.

*Fruit cavity*.—Absent or small/slight.

*Evenness of color of skin*.—Even or very slightly uneven.

*Evenness of color of flesh*.—Even.

*Fruit sweetness/taste*.—Subjective, described as consistently sweet with moderate acidity, average Brix° 2021=10.1.

*Fruit firmness of flesh*.—Firm.

*Fruit firmness of skin*.—Medium.

*Fruit weigh* (*secondary fruit*).—Average 16 grams.

*Fruit quantity*.—Average of 22.

*Fruit size*.—An average of 34 mm in length and width.

*Season of harvest*.—Everbearer, May through October, protected table-top culture, South East United Kingdom 2021 records from a March planting and deblossoming mid-May: 1st fruit produced on Jun. 24, 2021, 50% pick date: Aug. 16, 2021, last pick date Sep. 23, 2021.

*Achenes*.—11A in color when mature, 1.55 mm in length and 0.66 mm in diameter, smooth and glabrous surface, even coloration, 9B in color, 244 total number of seeds on one representative berry, position below surface.

*Longevity of fruit*.—3 to 5 days from fully ripe and held at 4° C.

*Shipping quality*.—Good, has been observed to exceed 5 days when subjected to typical supply chain conditions.

It is claimed:

1. A new and distinct cultivar of *Fragaria* plant named 'EMR 639' as herein illustrated and described.

* * * * *